US011547551B2

(12) United States Patent
Larkin et al.

(10) Patent No.: US 11,547,551 B2
(45) Date of Patent: Jan. 10, 2023

(54) ENGINEERED TENDON GRAFT FOR ROTATOR CUFF REPAIR

(71) Applicant: THE REGENTS OF THE UNIVERSITY OF MICHIGAN, Ann Arbor, MI (US)

(72) Inventors: Lisa M. Larkin, Ann Arbor, MI (US); Ellen M. Arruda, Ann Arbor, MI (US); Michael Smietana, Orion, MI (US); Asheesh Bedi, Ann Arbor, MI (US); Stoyna Novakova, Macomb, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 16/080,688

(22) PCT Filed: Mar. 2, 2017

(86) PCT No.: PCT/US2017/020447
§ 371 (c)(1),
(2) Date: Aug. 29, 2018

(87) PCT Pub. No.: WO2017/151919
PCT Pub. Date: Sep. 8, 2017

(65) Prior Publication Data
US 2019/0091007 A1    Mar. 28, 2019

Related U.S. Application Data

(60) Provisional application No. 62/302,581, filed on Mar. 2, 2016.

(51) Int. Cl.
*A61F 2/08* (2006.01)
*A61L 27/38* (2006.01)
(Continued)

(52) U.S. Cl.
CPC .............. *A61F 2/0811* (2013.01); *A61F 2/08* (2013.01); *A61K 35/32* (2013.01);
(Continued)

(58) Field of Classification Search
CPC ...... A61F 2/08; A61F 2/0805; A61L 27/3662; C12N 5/00
(Continued)

(56) References Cited

U.S. PATENT DOCUMENTS 5,441,508 A    8/1995   Gazielly et al.
7,422,900 B1   9/2008   Kosnik et al.
(Continued)

FOREIGN PATENT DOCUMENTS

CN    101795718 A    8/2010
CN    102316890 A    1/2012
(Continued)

OTHER PUBLICATIONS

Michael Smietana, Development and Manufacturing of Scaffoldless Constructs for Tendon/Ligament Repair, A dissertation submitted in partial fulfillment of the requirements for the degree of Doctor of Philosophy (Biomedical Engineering in the University of Michigan 2014) (Year: 2014).*
(Continued)

*Primary Examiner* — Bruce E Snow
(74) *Attorney, Agent, or Firm* — Reising Ethington P.C.

(57) ABSTRACT

The present disclosure relates to tissue engineering, and more particularly to a method for treating or repairing rotator cuff or other tendon tears or damage using scaffold-free 3-dimensional engineered tendon constructs.

6 Claims, 5 Drawing Sheets

(51) Int. Cl.
    C12N 5/077      (2010.01)
    A61K 35/32      (2015.01)
    A61L 27/36      (2006.01)
    A61F 2/00       (2006.01)
(52) U.S. Cl.
    CPC ....... *A61L 27/3662* (2013.01); *A61L 27/3687* (2013.01); *A61L 27/386* (2013.01); *A61L 27/3834* (2013.01); *C12N 5/066* (2013.01); *C12N 5/0669* (2013.01); *A61F 2/0095* (2013.01); *A61F 2002/087* (2013.01); *A61F 2220/0008* (2013.01); *A61F 2240/001* (2013.01); *A61F 2250/0067* (2013.01); *A61L 2430/10* (2013.01); *A61L 2430/40* (2013.01); *C12N 2500/33* (2013.01); *C12N 2501/115* (2013.01); *C12N 2501/999* (2013.01); *C12N 2513/00* (2013.01)

(58) Field of Classification Search
    USPC .................................. 623/13.11, 13.14, 13.2
    See application file for complete search history.

(56) References Cited

U.S. PATENT DOCUMENTS

| | | | |
|---|---|---|---|
| 8,080,260 B2* | 12/2011 | Derwin | A61L 27/3633 424/423 |
| 8,097,455 B2 | 1/2012 | Larkin et al. | |
| 8,202,318 B2* | 6/2012 | Willobee | A61F 2/08 623/13.11 |
| 8,764,828 B2 | 7/2014 | Arruda et al. | |
| 9,446,164 B2 | 9/2016 | Spedden et al. | |
| 9,463,263 B2 | 10/2016 | Zheng | |
| 2005/0255140 A1 | 11/2005 | Hagan et al. | |
| 2008/0021554 A1 | 1/2008 | Stone et al. | |
| 2010/0196347 A1 | 8/2010 | Kery | |
| 2011/0238179 A1* | 9/2011 | Laurencin | A61B 17/1146 623/13.19 |
| 2013/0018463 A1 | 1/2013 | Haddad et al. | |
| 2017/0037354 A1 | 2/2017 | Larkin et al. | |

FOREIGN PATENT DOCUMENTS

| | | |
|---|---|---|
| CN | 104274221 A | 1/2015 |
| JP | 2003-508130 A | 3/2003 |
| WO | WO-2011/052668 A1 | 5/2011 |
| WO | WO-2011/085920 A1 | 7/2011 |
| WO | WO-2014/141392 A1 | 9/2014 |

OTHER PUBLICATIONS

Alhadlaq et al., Mesenchymal stem cells: isolation and therapeutics, Stem Cells Dev., 13(4):43648 (Aug. 2004).

Benjamin et al., Where tendons and ligaments meet bone: attachment sites ('entheses') in relation to exercise and/or mechanical load, J. Anat., 208(4):471-90 (Apr. 2006).

Claudepierre et al., The entheses: histology, pathology, and pathophysiology, Joint Bone Spine, 72(1):32-7 (Jan. 2005).

Gronthos et al., A method to isolate and purify human bone marrow stromal stem cells, Methods Mol. Biol., 449:45-57 (2008).

International Application No. PCT/US2017/020447, International Preliminary Report on Patentability, dated Sep. 4, 2018.

International Application No. PCT/US2017/020447, International Search Report and Written Opinion, dated Jun. 27, 2017.

Lattouf et al., Picrosirius red staining: a useful tool to appraise collagen networks in normal and pathological tissues, J. Histochem. Cytochem., 62(10):751-8 (Oct. 2014).

Montgomery et al., Biologic augmentation of rotator cuff repair, Curr. Rev. Musculoskelet. Med., 4(4):221-30 (Dec. 2011).

Montgomery et al., Failed rotator cuff surgery, evaluation and decision making, Clin. Sports Med., 31(4):693-712 (Oct. 2012).

Pittenger et al., Mesenchymal stem cells and their potential as cardiac therapeutics, Circ. Res., 95(1):9-20 (Jul. 2004).

Ratcliffe et al., Scaffolds for tendon and ligament repair and regeneration, Ann. Biomed. Eng., 43(3):819-31 (Mar. 2015).

Vitale et al., Rotator cuff repair: an analysis of utility scores and cost-effectiveness, J. Shoulder Elbow Surg., 16(2):181-7 (Mar.-Apr. 2007).

Vogel et al., Determination of collagen content within picrosirius red stained paraffin-embedded tissue sections using fluorescence microscopy, MethodsX, 2:124-35 (Feb. 2015).

Waggett et al., Characterization of collagens and proteoglycans at the insertion of the human Achilles tendon, Matrix Biol., 16(8):457-70 (Mar. 1998).

Wolfe et al., Isolation and culture of bone marrow-derived human multipotent stromal cells (hMSCs), Methods Mol. Biol., 449:3-25 (2008).

Zhang et al., Analysis of rotator cuff repair trends in a large private insurance population, Arthroscopy, 29(4):623-9 (Apr. 2013).

Zhang et al., Arthroscopic versus open shoulder stabilization: current practice patterns in the United States, Arthroscopy, 30(4):436-43 (Apr. 2014).

Zhou et al., Combined marrow stromal cell-sheet techniques and high-strength biodegradable composite scaffolds for engineered functional bone grafts, Biomaterials, 28(5):814-24 (Feb. 2007).

Office action issued by the the China National Intellectual Property Administration (CNIPA) for application 201780027250.6 dated Jun. 3, 2021; 6 pages.

Office action with English translation issued by the the China National Intellectual Property Administration (CNIPA) for application No. 201780027250.6 dated Oct. 18, 2021; 9 pages.

Metadata for Smietana reference from University of Michigan Library, accessed Nov. 30, 2021; accession date Oct. 13, 2014, Development and Manufacturing of Scaffold-less Contstructs for Tendon/Ligament Repair.

"Thesis Withholding," University of Illinois Office of Technology Management, accessed Nov. 30, 2021, date Nov. 2012.

Office action with English translation issued by the the Japanese Patent Office for application No. 2018-545859 dated Sep. 13, 2022; 6 pages.

* cited by examiner

FIGURES 4E-4K
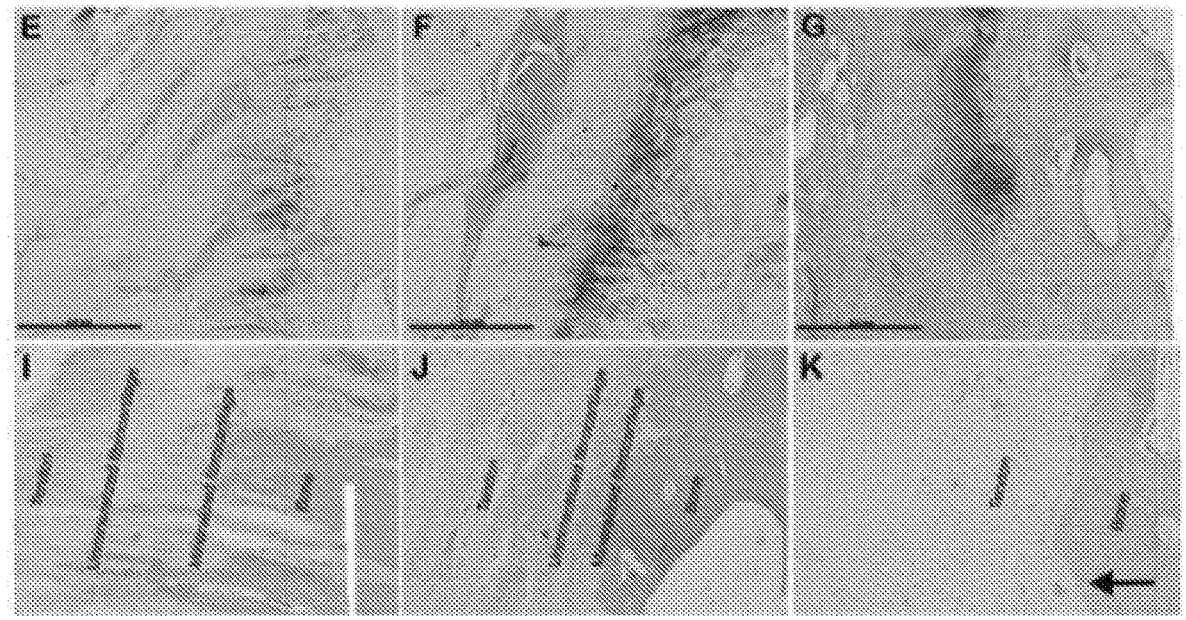
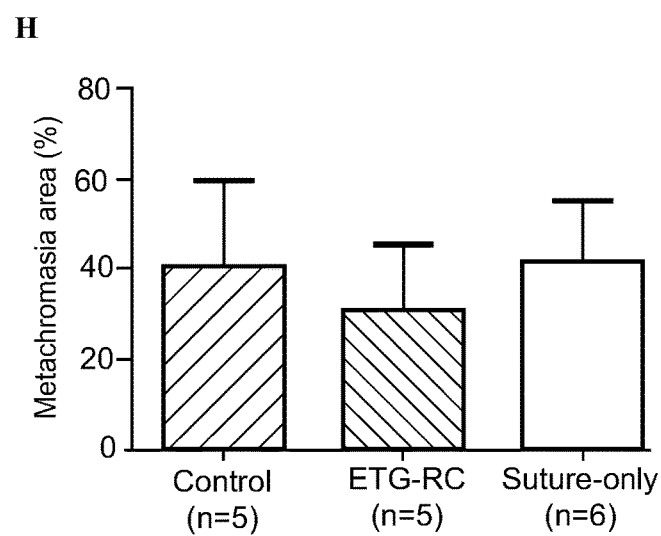

ENGINEERED TENDON GRAFT FOR ROTATOR CUFF REPAIR

CROSS-REFERENCE TO RELATED APPLICATIONS

This application is a National Stage Application of International Patent Application No. PCT/US2017/020447, filed Mar. 2, 2017, which claims the priority benefit of U.S. Provisional Patent Application No. 62/302,581, filed Mar. 2, 2016, which is incorporated by reference in its entirety.

FIELD OF THE INVENTION

The present disclosure relates to tissue engineering, and more particularly to scaffold-free tendon construct(s) and methods for treating tendon, e.g., rotator cuff, tears or damage, using implantable scaffold-free tendon construct(s).

BACKGROUND

A tendon is a fibrous connective tissue that attaches muscle to bone. A tendon serves to move the bone or structure to which it is attached (Vorvick et al. Medline Plus, U.S. NLM, 2014).

Rotator cuff (RC) tears are one of the most common orthopedic disorders in the US with over 75,000 repair procedures performed annually (Vitale et al., J. Shoulder and Elbow Surg 16(2):181-197 (2007) and a health care cost estimated at $30 billion dollars annually. Healing RC tears with current suture or augmented scaffold techniques fails to regenerate the native tendon bone interface and instead forms a weaker fibrovascular scar that is prone to failure. The regeneration of this interface is critical to improving clinical outcomes.

To date, the standard for rotator cuff repair is single or double row suture technique. Repair of RC with suture techniques fails 20-57% of the time due to the lack of regeneration of the native tendon to bone interface or "enthesis" (Montgomery et al., Clin Sports Med. 31(4):693-712, 2012; Montgomery et al., Curr Rev Musculoskelet Med. 4(4):221-30, 2011; Zhang et al., Arthroscopy 30(4): 436-43, 2014; Zhang et al., Arthroscopy 29(4):623-29, 2013). Currently, 42% of the RC repairs (30,000/year) are mechanically reinforced with biological or synthetic patches. The efficacy of the commonly used biological patches, is dismal with re-tear rates near 91% (Ratcliffe et al., Ann Biomed Eng. 43(3):819-31, 2015). The regeneration of the enthesis is critical to improving clinical outcomes.

SUMMARY OF THE INVENTION

Provided herein is a scaffold-free, three-dimensional (3-D) tissue Engineered Tendon Graft designed for Rotator Cuff repair (ETG-RC) for repair of the tendon in a rotator cuff repair procedure, and methods and systems for making a rotator cuff repair construct. The construct is also useful in repair of other damaged tendons. The construct herein provides for fixation of the tendon construct at one end to bone during tendon repair and provides at the opposite end for fixation to tendon during tendon repair, giving a fully integrated tissue structure that shows signs of enthesis formation in vivo.

In various embodiments, the disclosure provides a rotator cuff repair construct that is a tendon construct, comprising: i) a bone-fixation end, wherein the bone-fixation end comprises a single column of tendon tissue for fixation to bone in a tendon repair surgery and at the opposite end the column branches to form a tendon-fixation end of the tendon construct, and ii) a tendon-fixation end having two or more tendon prongs each having a free end for fixation to a tendon in a tendon repair surgery and at the opposite end the prong ends fuse to form one end of the bone-fixation end of the construct. It is contemplated that the tendon construct is a scaffold-free, three dimensional tissue construct. It is also contemplated that the tendon repair construct is a tendon repair construct for repair of other damaged tendons, not just rotator cuff.

In various embodiments, the tendon-fixation end has 2, 3, 4 or 5 prongs.

In various embodiments, the bone-fixation end has a diameter of approximately 3-6 mm. In various embodiments, the diameter of each of the tendon-fixation end prongs is approximately 2-3 mm.

In various embodiments, the total length of the tendon construct is from about 4 cm to about 10 cm. In various embodiments, the tendon-fixation end prongs start at about one-half (½) to two-thirds (⅔) of the length of the entire tendon construct. In various embodiments, the bone-fixation end is from about 2-7 cm in length. In various embodiments, the length of each of the tendon-fixation end prongs is approximately 1-5 cm.

In one embodiment, the bone-fixation end is approximately 2-7 cm in length and 3-6 mm in diameter and the tendon-fixation end is approximately 1-5 cm in length and 2-3 mm in diameter. In various embodiments, the tendon construct comprises a bone-fixation end and three tendon prongs at the tendon-fixation end.

In various embodiments, the disclosure provides a method for treating or repairing a rotator cuff tear in a subject, comprising: a) making a rotator cuff repair construct that is a tendon construct comprising i) a bone-fixation end, wherein the bone-fixation end comprises a single column of tendon tissue for fixation to bone in a tendon repair surgery and at the opposite end the column branches to form a tendon-fixation end of the tendon construct, and ii) a tendon-fixation end having two or more tendon prongs each having a free end for fixation to a tendon in a tendon repair surgery and at the opposite end the prong ends fuse to form one end of the bone-fixation end of the construct; and b) implanting the rotator cuff repair construct into a site of damaged or torn rotator cuff.

In various embodiments, the method further comprises using a baseball stitch to allow for passage of the rotator cuff repair construct into the damaged tendon and into a bone tunnel. It is contemplated that the bone-fixation end is passed through a bone tunnel and sutured to periosteum at the end distal during the tendon repair in vivo and the tendon-fixation end prongs are sutured to tendon in vivo.

In various embodiments, the rotator cuff repair construct has been frozen prior to implantation. In various embodiments, the rotator cuff repair construct is frozen at—a range between −70° C. or −80° C.±5° C. In various embodiments, the rotator cuff repair construct is allowed to thaw at 4° C. for up to 3 hours prior to implantation. In various embodiments, the rotator cuff repair construct is allowed to thaw at 4° C. for 1, 2 or 3 hours prior to implantation.

It is contemplated that the method for rotator cuff repair using the tendon construct described herein is useful for any tendon in which suture repair is commonly performed. The disclosure herein provides for a tendon repair construct, or tendon suture repair construct, having the characteristics set forth for the rotator cuff repair construct, e.g., having a bone-fixation end and tendon-fixation end as described herein. Also provided is a method of repairing tendon comprising implanting a tendon repair construct as described herein. Also contemplated is a method and system for making a tendon repair construct, or tendon suture repair construct, having the characteristics described herein, e.g., having a bone-fixation end and a tendon-fixation end as described herein.

In various embodiments, the repair is of tendon in the rotator cuff, including supraspinatus, infraspinatus, subscapularis and teres minor tendon. Other tendons that may be repaired in a tendon repair using the present method include, but are not limited to Achilles tendon, finger or hand tendon, flexor tendons, extensor tendons, peroneal tendon, biceps, triceps, patella, elbow, and other tendons in the ankle, knee, hand, foot, or shoulder.

In various embodiments, the rotator cuff repair construct establishes an enthesis in vivo after implantation. In various embodiments, the rotator cuff implant exhibits aligned collagen fibrils in vivo.

In one embodiment, the impairment of the rotator cuff or other tendon is reduced by approximately 10%, 15%, 20%, 25%, 30%, 35%, 40%, 45%, 50% or more compared to an untreated subject. In one embodiments, mobility and/or strength of the rotator cuff is improved by 1.5, 2, 2.5, 3, 4, 5, 6, 7, 8, 9, 10 fold or more. Impairment and mobility are measured using techniques known to those skilled in the field.

In various embodiments, the subject in need is a mammal. In various embodiments, the subject is human.

Also contemplated herein is a method of forming a rotator cuff repair construct that is a tendon construct having a bone-fixation end and a tendon-fixation end comprising: (a) placing bone marrow stromal cells on a substrate in a fibrogenic growth medium without placing the cells in an exogenous scaffold and allowing the cells to form a confluent tendon monolayer, wherein a three-dimensional tendon construct is formed via detachment of the monolayer from the substrate; (b) allowing a single tendon construct to grow in culture until the three dimensional tendon construct is approximately 1-2 mm in diameter and 4-10 cm in length; (c) placing two or more single tendon constructs side by side length-wise in culture in fibrogenic differentiation medium such that approximately one-half (½) to two-thirds (⅔) of the length of the two or more tendon constructs fuse together to become the bone-fixation end of the repair construct for attachment to bone, and the remaining approximately ½ to one-third (⅓) of the tendon constructs are kept for formation of individual tendon prongs for the tendon-fixation end of the repair construct.

In various embodiments, six single tendon constructs are placed in culture, and the bone-fixation end is formed by fusing all six single constructs at one end and the tendon-fixation end is formed by pairing two tendon constructs together to form a single tendon prong, in this case resulting in three prongs, in the tendon-fixation end of the construct.

In various embodiments, the rotator cuff construct comprising the tendon construct has 2, 3, 4 or 5 tendon prongs at the tendon-fixation end. In various embodiments, the tendon construct has 3 tendon prongs at the tendon-fixation end.

In various embodiments, the rotator cuff repair construct is allowed to grow in culture for at least 6 weeks. For example, the repair construct may be allowed to grow in culture for 6, 7 or 8 weeks.

In various embodiments, the method further comprises freezing the rotator cuff repair construct at −80° C.±5° C.

In various embodiments, the method further comprises freezing the rotator cuff repair construct at −80° C.±5° C. after growth in culture for at least 6-8 weeks.

In various embodiments, the fibrogenic growth medium includes one or more of basic fibroblast growth factor, dexamethasone, ascorbic acid-2-phosphatase and L-proline. In various embodiments, the fibrogenic differentiation medium includes one or more of, dexamethasone, ascorbic acid-2-phosphatase, L-proline and transforming growth factor beta.

Also provided is a system for forming a rotator cuff repair construct that is a tendon construct comprising: a) a substrate; b) bone marrow stromal cells provided on the substrate without disposing the cells in an exogenous scaffold; c) a fibrogenic growth medium provided in contact with the bone marrow stromal cells which causes the cells to generate an extracellular matrix when cultured in vitro and to self-organize to form a confluent tendon monolayer; wherein a three-dimensional tendon construct is formed via detachment of the monolayer from the substrate; d) placing two or more tendon constructs formed in (c) side by side lengthwise in culture in fibrogenic differentiation medium such that one-half (½) to two-thirds (⅔) of the length of the two or more constructs fuse together to become the bone-fixation end of the repair construct and the remaining approximately ½ to ⅓ of the tendon constructs are kept for formation of individual tendon prongs for the tendon-fixation end of the repair construct. Optionally, in (d) six tendon constructs are placed in culture, and the bone-fixation end is formed by fusing all six constructs and the tendon-fixation end is formed by pairing two tendon constructs together to form one tendon prong of the tendon prongs in the tendon-fixation end of the construct.

In various embodiments of the system, the total length of the tendon construct is from about 4 cm to about 10 cm. In various embodiments of the system, the tendon-fixation end prongs start at about one-half (½) to two-thirds (⅔) of the length of the entire tendon construct. In various embodiments of the system, the bone-fixation end is from about 2-7 cm in length. In various embodiments of the system, the length of each of the tendon-fixation end prongs is approximately 1-5 cm.

In various embodiments of the system, the bone-fixation end has a diameter of approximately 3-6 mm. In various embodiments of the system, the diameter of each of the tendon-fixation end prongs is approximately 2-3 mm.

In one embodiment, the bone-fixation end is approximately 2-7 cm in length and 3-6 mm in diameter and the tendon-fixation end is approximately 1-5 cm in length and 2-3 mm in diameter.

In various embodiments of the system, the rotator cuff construct comprising the tendon construct has 2, 3, 4 or 5 tendon prongs at the tendon-fixation end. In various embodiments, the tendon construct has 3 tendon prongs at the tendon-fixation end.

In various embodiments of the system, the fibrogenic growth medium includes one or more of basic fibroblast growth factor, dexamethasone, ascorbic acid-2-phosphatase and L-proline. In various embodiments of the system, the fibrogenic differentiation medium includes one or more of dexamethasone, ascorbic acid-2-phosphatase, L-proline and transforming growth factor beta.

The system also includes at least two anchors secured to the substrate in spaced relationship. In various embodiments, each construct in culture is held by an anchor at one or more places during formation of the 3-D construct. The system further includes a differentiation medium including cells in culture, comprising one or more of ascorbic acid-2-phosphatase, L-proline, transforming growth factor beta (TGF-β) and/or dexamethasone, provided on the substrate, where at least some of the 3-D tissue is in contact with the anchors. The cells are cultured in vitro under conditions to allow the cells to become confluent and self-organize into a 3-D tissue, and the anchors capture the monolayer as it detaches from the substrate to form the three-dimensional tendon construct.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus. Although the applicant(s) invented the full scope of the invention described herein, the applicants do not intend to paragraph subject matter described in the prior art work of others. Therefore, in the event that statutory prior art within the scope of a paragraph is brought to the attention of the applicant(s) by a Patent Office or other entity or individual, the applicant(s) reserve the right to exercise amendment rights under applicable patent laws to redefine the subject matter of such a paragraph to specifically exclude such statutory prior art or obvious variations of statutory prior art from the scope of such a paragraph. Variations of the invention defined by such amended paragraphs also are intended as aspects of the invention.

BRIEF DESCRIPTION OF THE DRAWINGS

FIGS. 4A-4K show Collagen Alignment, Fibrocartilage Formation, and H&E at Enthesis. Picrosirius stained enthesis (FIG. 4A) Contralateral shoulder, (FIG. 4B) ETG-RC repair, (FIG. 4C) Suture only repair. Images visualized under polarized light and imaged at X4 magnification. (FIG. 4D) Mean gray-scale values. (#) Denotes statistical significance compared to contralateral shoulder (p<0.05). (*) Denotes statistical significance compared to ETG shoulder. Error bars represent+/−SD. Metachromasia stained fibrocartilage Formation at Enthesis. (FIG. 4E) Contralateral shoulder, (FIG. 4F) ETG-RC repair, (FIG. 4G) Suture only repair. Images were taken at ×4 magnification. (FIG. 4H) Percent of metachromasia at the enthesis. H&E stained enthesis (FIG. 4I) Contralateral shoulder, (FIG. 4J) ETG-RC repair, (FIG. 4K) Suture only repair. Arrows points to tendon-bone interface.

DETAILED DESCRIPTION

Figure 1A:
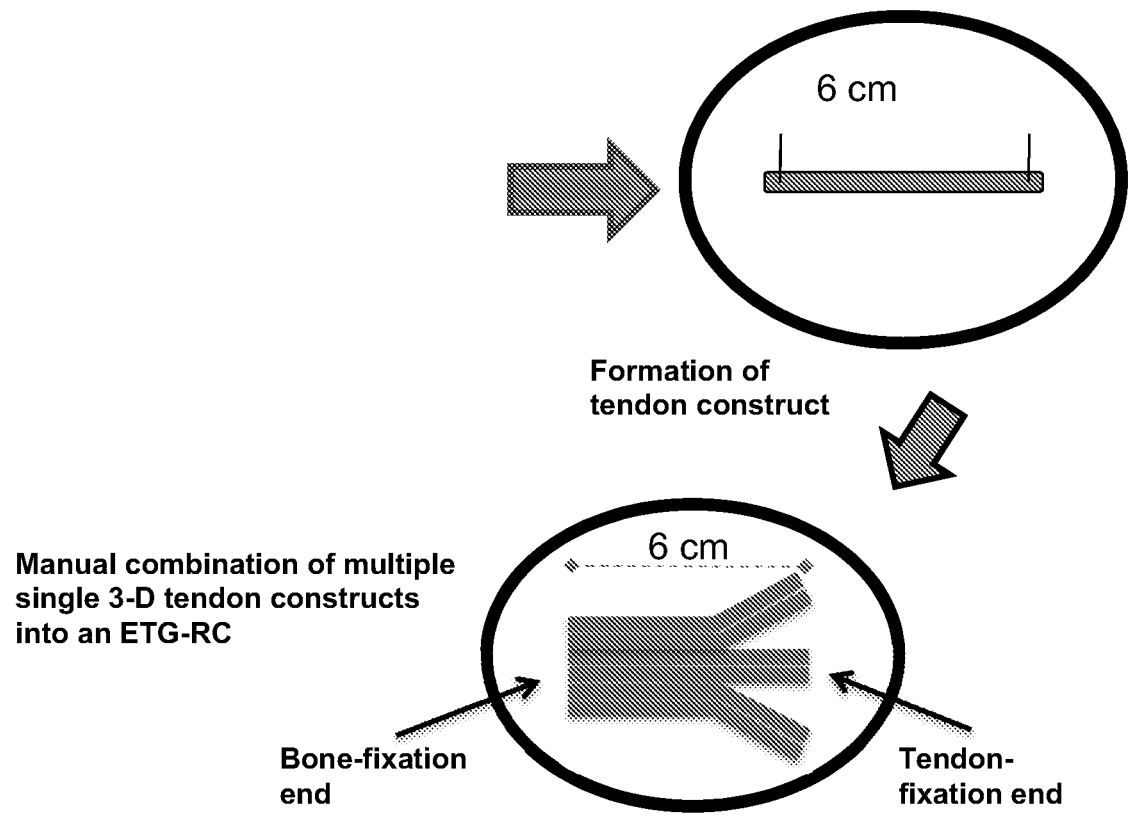
FIG. 1A is a schematic diagram of an exemplary process for forming the rotator cuff repair construct.

Provided herein is a scaffold-free, three-dimensional tissue Engineered Tendon Graft designed for Rotator Cuff repair (ETG-RC) for repair of the tendon in a rotator cuff tear-repair procedure, and methods and systems for making a rotator cuff repair construct. The construct herein provides for fixation of the tendon construct at one end to bone during tendon repair and provides at the opposite end for fixation to tendon during tendon repair, giving a fully integrated tissue structure that shows signs of enthesis formation in vivo.

Unless otherwise stated, the following terms used in this application, including the specification and claims, have the definitions given below.

As used in the specification and the appended claims, the indefinite articles "a" and "an" and the definite article "the" include plural as well as singular referents unless the context clearly dictates otherwise.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, or 0.05% of a given value or range. Whenever the term "about" or "approximately" precedes the first numerical value in a series of two or more numerical values, it is understood that the term "about" or "approximately" applies to each one of the numerical values in that series.

The terms "ambient temperature" and "room temperature" are used interchangeably herein and refer to the temperature of the surrounding environment (e.g., the room in which a reaction is conducted or a composition is stored). In certain embodiments, ambient temperature or room temperature is a range from about 15° C. to about 28° C., or from about 15° C. to about 25° C., or from about 20° C. to about 28° C., or from about 20° C. to about 25° C., or from about 22° C. to about 28° C., or from about 22° C. to about 25° C. The term "freezing" or "frozen" refer to the temperature of the surrounding environment that is less than 0° C., including −20° C., −70° C. and −80° C.

As used herein, the term "treatment" (also "treat" or "treating") refers to implanting a rotator cuff repair construct or tendon construct that partially or completely alleviates, ameliorates, relieves, reduces severity of and/or reduces incidence of one or more symptoms or features of rotator cuff or tendon injury, whether acute injury or injury due to a degeneration or a particular disease, disorder, and/or condition.

As used herein, to "repair" or "retard" tendon damage or tear, such as rotator cuff damage or a rotator cuff tear refers to a method to treat a site of injury or damage in an area of tendon, e.g., rotator cuff. Damage refers to a tear, abrasion, lesion or other aberration or wound in the tendon structure of the rotator cuff in a subject compared to normal, non-damaged rotator cuff tendon. In some embodiments, damage arises from a trauma to the rotator cuff or areas surrounding the rotator cuff such that the rotator cuff is damaged. In other embodiments, the rotator cuff damage arises from degeneration of the rotator cuff due to normal degradation over time or due to a degenerative disorder. To repair rotator cuff or tendon damage is to partially or completely heal the wound in the rotator cuff. To retard damage is to curtail or slow the initial damage from progressing in the rotator cuff or tendon, thereby preventing further damage. To prevent further damage is to slow or stop the progression of damage in the rotator cuff or tendon such that no significant additional damage is observed in the site.

Figure 1B:
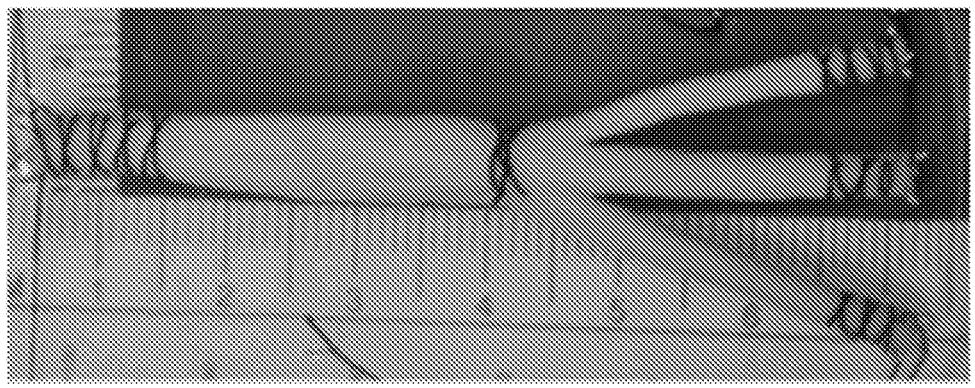
FIG. 1B shows the rotator cuff construct consisting of six linear tendon tissues fused together at the bone-fixation end and having three prongs and the tendon-fixation end.

A "tendon construct" as used herein refers to a construct derived from cells in culture that form a 3-dimensional construct having properties of tendon, and which has at one end, the bone-fixation end, a single cylinder of tendon tissue for fixation to a bone in a tendon repair process, and having at its opposite end, the tendon-fixation end, separate bundles or prongs of tendon-like tissue for fixation to tendon during a tendon repair process. It is contemplated that the tendon prongs in the tendon end originate from, are derived from or branch from the tissue in the bone-fixation end of the construct that is opposite from the bone-fixation end of the construct that will be fixed to bone during tendon repair surgery. Additionally, when forming the tendon construct, it can also be seen that the tendon-fixation end prongs are fused at one end to form, or fuse to, one end of the bone-fixation end of the construct. A representation of the tendon construct is set out in FIG. 1A and FIG. 1B. In various embodiments, the tendon construct has 2, 3, 4 or 5 tendon prongs for fixation in vivo.

The cells for use in culture to form a tendon construct include cells that are pluripotent and can form tendon cells when cultured with appropriate media, including but not limited to, bone marrow stromal cells, other precursor stem cells, and adipose stem cells, as well as primary tendon fibroblasts.

Rotator Cuff Injuries and Tendon Repair

The rotator cuff is a network of four muscles that come together as tendons to form a covering around the head of the humerus bone in the arm. The four tendons include the supraspinatus tendon, the infraspinatus tendon, the subscapularis tendon and the teres minor tendon. The majority of tears in the human occur in the supraspinatus muscle and tendon, but other parts of the rotator cuff may also be torn or damaged.

Contemplated herein is treatment or repair of a rotator cuff tear or other damage to a tendon. A rotator cuff tear can be either a partial tear, which damages the rotator cuff, but does not completely sever it, or a full-thickness, or complete, tear, which splits the soft tissue into two pieces and can essentially leave a hole in the tendon. A large tear is considered a tear of greater than 3 cm. A tear can be the result of an acute injury or from repetitive or degenerative damage to one or more of the tendons in the rotator cuff.

Subjects receiving rotator cuff treatment or repair as contemplated herein include mammals, such as humans, non-human primates such as chimpanzees, and other apes and monkey species; farm animals such as cattle, horses, sheep, goats, swine; domestic animals such as dogs, and cats; laboratory animals including rodents, such as rats, mice and guinea pigs, and the like.

In one embodiment, the impairment of the rotator cuff or tendon is reduced by approximately 10%, 15%, 20%, 25%, 30%, 35%, 40%, 45%, 50% or more compared to an untreated subject. In one embodiments, mobility and/or strength of the rotator cuff or tendon is improved by 1.5, 2, 2.5, 3, 4, 5, 6, 7, 8, 9, 10 fold or more. Impairment and mobility are measured using techniques known to those skilled in the field.

In various embodiments, the bone-fixation end of the tendon construct has a diameter of approximately 3-6 mm, e.g., approximately 3, 4, 5, or 6 mm. In various embodiments, the diameter of each of the tendon-fixation end prongs is approximately 2-3 mm, e.g., 2 or 3 mm.

In various embodiments, the total length of the construct is from 4-10 cm in length. In various embodiments, the bone-fixation end is from about 2-7 cm in length, e.g., approximately 2, 3, 4, 5, 6 or 7 cm in length. In various embodiments, the length of each of the tendon-fixation end prongs is approximately 1-5 cm, e.g., 1, 2, 3, 4 or 5 cm.

In various embodiments, the tendon-fixation end prongs of the tendon construct start at about one-half (½) to two-thirds (⅔) of the length of the entire tendon construct. An exemplary tendon construct is depicted in FIG. 1.

In various embodiments, the tendon construct may be modified for the subject being treated, e.g., it may be made smaller or large in length or width depending on the size of the rotator cuff insertion site in the subject.

In one embodiment, the bone-fixation end of the tendon construct is approximately 2-7 cm in length and 3-6 mm in diameter and the tendon-fixation end is approximately 1-5 cm in length and 2-3 mm in diameter, optionally the construct has three tendon prongs at the tendon-fixation end.

In one embodiment, a rotator cuff repair construct can be used in combination with one or more other active agents useful for treating or ameliorating rotator cuff damage. The other active agent(s) can enhance the effects of the rotator cuff repair construct and/or exert pharmacological effects in addition to those of the rotator cuff repair construct. Active agents include anti-inflammatory compounds, such as aspirin, NSAIDS and cortisone.

The disclosure also provides that other tendons in addition to rotator cuff tendons may be repaired in a tendon repair using the present tendon construct and method. Exemplary tendons, include, but are not limited to Achilles tendon, finger or hand tendon, flexor tendons, extensor tendons, peroneal tendon, biceps, triceps, patella, elbow, and other tendons in the ankle, knee, hand, foot, or shoulder.

Tendon

The interface between bone and tendon is referred to as an enthesis. The purpose of the enthesis tissue is to transmit loads with high fidelity over a minimal volume of tissue from the compliant tendon to the stiff bone at the bone-tendon interface. This tissue is composed of four different zones that aid in the transition between the two vastly different tissues. The four zones of the enthesis are tendon, unmineralized fibrocartilage, mineralized fibrocartilage, and bone. The transition from tendon to unmineralized fibrocartilage is gradual, whereas a distinct boundary exists between unmineralized and mineralized fibrocartilage in adult tissue. This boundary is termed a tidemark and can be identified using hematoxylin and eosin (H & E) staining due to its extreme basophilic nature (Claudepierre and Voisin, Joint Bone Spine 72: 32, 2005; Benjamin et al., J Anat 208: 471, 2006. Fibrocartilage zones are composed of type II collagen and proteoglycans such as aggrecan, biglycan and decorin. The cells in fibrocartilage have the phenotype of chondrocytes, round and arranged in pairs or rows within lacunae. There are no molecular markers that are unique to this type of tissue, however, fibrocartilage, and in general the enthesis, is generally characterized by the presence of type II collagen due to the fact that this protein is not present in the neighboring ligament and bone tissues (Waggett et al., Matrix Biol 16: 457, 1998).

Tendons are highly organized connective tissues that transmit forces between muscle and bone. They are resilient during the development of tension but flexible enough to conform to their mechanically demanding environment. The mechanical integrity of tendon tissue can be attributed to the parallel fibrils of collagen. In the resting state, the collagen fibrils take on a wavy conformation, defined as the crimp. As a tendon is stretched, the crimped collagen fibrils begin to straighten out, and as a result, the tendon becomes stiffer with increasing application of mechanical strain.

Native tendons possess an extracellular matrix (ECM) composed of many proteins, glycosaminoglycans, and proteoglycans that control the assembly of the load-bearing collagen fibril and contribute to the formation of the tissue hierarchy. Fibroblasts rely on cell-matrix signaling pathways during development to properly assemble the fibrils and maintain form and function after maturation. Previous attempts have been made to create biologically based tendons in vitro, but these have met with limited success because of the difficulty in creating a construct that is both mechanically and biologically compatible with the in vivo environment. See e.g., U.S. Pat. No. 8,097,455.

Self-organized 3-D tendon has been engineered from cells isolated from rat Achilles tendons (U.S. Pat. No. 7,422,900). Primary tendon fibroblasts secrete and organize their own ECM and under the right conditions, and self-assemble into cylindrical constructs without the aid of exogenous scaffolding. The resulting scaffold-free tissue is composed of aligned, small-diameter (50 nm) collagen fibrils, a large number of cells, and an excess of non-collagenous ECM-all characteristics of embryonic tendon. The stress-strain response of the constructs also resembles the non-linear behavior of immature tendons, and the ultimate tensile strength is approximately equal to that of embryonic chick tendon, roughly 2 MPa.

Engineered Tissue Constructs

Single layer cell sheets grown from bone marrow stromal cells (BMSC) and wrapped around composite scaffolds have recently been shown to form constructs that resemble bone in vitro and in vivo (Zhou et al., Biomaterials 28: 814, 2007). However, this method still involves the use of exogenous scaffolding that must incorporate into native tissue. Therefore, while scaffolding strategies appear to promote osteogenic or fibroblastic cell growth, limitations such as immune rejection, degradation, and nonphysiological mechanical properties of the scaffold need to be considered when used for bone, tendon and ligament repair.

BMSC are multipotent, mesenchymal stem cells that can differentiate into bone, cartilage, tendon, ligament, adipose tissue, and muscle (Alhadlaq and Mao, Stem Cells Dev 13: 436, 2004; Pittenger and Martin, Circ Res 95: 9, 2004) in response to chemical signals and generate and mineralize their own autogenous ECM. BMSC can be easily isolated from autologous and allogeneic sources and therefore serve as an attractive candidate for tissue engineering.

In various embodiments, BMSC isolation and expansion may be accomplished as follows. Under aseptic conditions, bone marrow may be collected from a bone of a host. For example, isolation of human BMSC is described in Gronthos et al., (Methods Mol Biol. 449:45-57, 2008) and Wolfe et al., (Methods Mol Biol. 449:3-25, 2008). In certain embodiments, sheep or other animal cells are isolated, in such cases, bone marrow stromal cells from bone marrow aspirations are isolated using a commercially available, Ficoll-Plaque kit from GE Healthcare (Ficoll-Paque PREMIUM: 28-4039-56AC), and plated onto tissue culture plates that have been altered to contain constraint pins used for capturing the monolayer as it forms a 3-D construct in GM for 72 hours. Additional methods for growing cells in culture are set out in the Examples.

The mitogenic effects of bFGF in addition to dexamethasone in the culture may increase proliferation, thus allowing for monolayer formation rather than the formation of nodules. TGF-β may be the factor that controls 2D versus 3D construct formation. Although the overall effects of this growth factor on BMSC are not fully known, it is generally used in culture to stimulate collagen production, matrix maturation, and/or to induce chondrogenic differentiation from BMSC. TGF-β may increase the rate of collagen production at an early stage of tendon construct development and prior to full osteogenic differentiation.

As described above, since BMSC are multipotent cells that can differentiate into a plurality of tissue types, several markers are used to identify tissues in the developing constructs according to the present invention. Type I collagen, fibronectin and elastin immunostaining are used as markers of tendon development. Morphological observations of cellular and ECM structures using light and electron microscopy may be used to identify the presence of the expected cell and tissue types in the developing constructs.

Formation of a bone-ligament-bone construct was described previously in U.S. Pat. No. 8,764,828, incorporated herein by reference.

Contemplated by the disclosure is a method of forming a rotator cuff repair construct that is a tendon construct having a bone-fixation end and a tendon-fixation end comprising: (a) placing bone marrow stromal cells on a substrate in a fibrogenic growth medium without placing the cells in an exogenous scaffold and allowing the cells to form a confluent tendon monolayer, wherein a three-dimensional tendon construct is formed via detachment of the monolayer from the substrate; (b) allowing a single tendon construct to grow in culture until the three dimensional tendon construct is approximately 1-2 mm in diameter and 4-10 cm in length; (c) placing two or more single tendon constructs side by side length-wise in culture in fibrogenic differentiation medium such that approximately one-half (½) to two-thirds (⅔) of the length of the two or more tendon constructs fuse together to become the bone-fixation end of the repair construct for attachment to bone, and the remaining approximately ½ to one-third (⅓) of the tendon constructs are kept, or used, for formation of individual tendon prongs for the tendon-fixation end of the repair construct.

Also provided is a system for forming a rotator cuff repair construct that is a tendon construct comprising: a) a substrate; b) bone marrow stromal cells provided on the substrate without disposing the cells in an exogenous scaffold; c) a fibrogenic growth medium provided in contact with the bone marrow stromal cells which causes the cells to generate an extracellular matrix when cultured in vitro and to self-organize to form a confluent tendon monolayer; wherein a three-dimensional tendon construct is formed via detachment of the monolayer from the substrate; d) placing two or more tendon constructs formed in (c) side by side lengthwise in culture in fibrogenic differentiation medium such that one-half (½) to two-thirds (⅔) of the length of the two or more constructs fuse together to become the bone-fixation end of the repair construct and the remaining approximately ½ to ⅓ of the tendon constructs are kept, or used, for formation of individual tendon prongs for the tendon-fixation end of the repair construct. Optionally, in (d) six tendon constructs are placed in culture, and the bone-fixation end is formed by fusing all six constructs and the tendon-fixation end is formed by pairing two tendon constructs together to form one tendon prong of the tendon prongs in the tendon-fixation end of the construct.

In various embodiments of the method or system, the total length of the tendon construct is from about 4 cm to about 10 cm. In various embodiments, the tendon-fixation end prongs start at about one-half (½) to two-thirds (⅔) of the length of the entire tendon construct. In various embodiments, the bone-fixation end is from about 2-7 cm in length. In various embodiments of the system, the length of each of the tendon-fixation end prongs is approximately 1-5 cm. The tendon construct may comprise 2, 3, 4 or 5 prongs at the tendon-fixation end.

Kits

Also contemplated herein are kits which comprise one or more tendon constructs useful in the method of the invention packaged in a manner which facilitates their use to practice methods. In one embodiment, such a kit includes a pre-formed rotator cuff repair construct comprising a tendon construct as described herein. In one embodiment, the kit comprises a plurality of tendon constructs for placement in culture in lengthwise succession for forming a rotator cuff repair construct in vitro. Optionally, the kit includes media for growing the tendon construct in vitro. In various embodiments, the rotator cuff repair construct or tendon constructs are frozen for shipment. The kit may further include a device suitable for implanting the rotator cuff repair construct according to a specific route of administration.

Additional aspects and details of the invention will be apparent from the following examples, which are intended to be illustrative rather than limiting.

EXAMPLES

Example 1. Generation of a Rotator Cuff Tendon Repair Construct

In various embodiments, BMSC isolation and expansion may be accomplished as follows. Under aseptic conditions, bone marrow may be collected from a bone of a host as known in the art and described herein using aspiration methods or other techniques. Tendon constructs are formed using a modification of previously described methods (see U.S. Pat. No. 8,764,828).

For the construct generation, all solutions and media were prepared and stored at 4° C. and were warmed to 37° C. in a heated bead bath prior to use. Growth medium (GM) consisted of 78% Dulbecco's modified Eagle medium (DMEM; Gibco, Grand Island, N.Y., USA), with 20% fetal bovine serum (FBS; Gibco, Grand Island, N.Y., USA), 2% antibiotic anti-mycotic (ABAM; Grand Island, N.Y., USA), $10^{-8}$ M dexamethasone (DEX; Sigma-Aldrich, St. Louis, Mo., USA), 6 ng/ml basic fibroblast growth factor (bFGF; Peprotech, Rocky Hill, N.J., USA), 0.13 mg/mL ascorbic acid-2-phosphatase (Sigma-Aldrich, St. Louis, Mo.), and 0.05 mg/mL L-proline (Sigma-Aldrich, St. Louis, Mo., USA). Differentiation medium (DM) consisted of 91% DMEM, 7% horse serum albumin (HS; Gibco, Grand Island, N.Y., USA), 2% ABAM, $10^{-8}$ M dexamethasone (DEX; Sigma-Aldrich, St. Louis, Mo., USA), 0.13 mg/mL asc-2-phos, 0.05 mg/mL L-proline, and 2 ng/mL transforming growth factor beta (TGF-β; Peprotech, Rocky Hill, N.J., USA).

The BMSCs were induced to a tendon lineage. Briefly, passage (3-4) cells were seeded at a density of 21,000 cells/cm$^2$ and fed with GM every other day. Six days after plating the GM was then replaced with DM and the monolayer was cultured for an additional 5 days. The monolayers spontaneously self-delaminate approximately 4-5 days following the switch to DM. The BMSCs were plated onto tissue culture plates that have been altered to contain constraint pins used for capturing the monolayer as it forms a 3-D construct. Following 3-D formation, the single constructs 1-2 mm in diameter and 6-8 cm in length were transferred from the original cell plate to a sylgard plate with constraint pins. Briefly, 100 mm diameter cell culture plates were filled with 15 ml Sylgard (Dow Chemical Corp., Midland, Mich., USA; type 184 silicon elastomer) and allowed to cure for 3 weeks at room temperature. Prior to use, plates were decontaminated with UV light (wavelength 253.7 nm) for 60 min and rinsed with 70% EtOH and DPBS.

Six of these single tendon constructs were placed side-by-side and allowed to fuse at one end, however approximately ⅔ of the way (4 cm) down the construct, the six constructs were split into three ends (two constructs each); creating a three-pronged region approximately 3 cm in length (FIG. 1). The DM media was changed every 2-3 days. After 7 weeks in vitro the tendon construct was fully formed. Prior to freezing, approximately 5-10 mm of all ends of the rotator cuff construct were sutured with baseball stitch using non-absorbable 5-0 silk suture. 6 inches of extra suture was left at the ends of each baseball stitch. After applying suture, the fully formed rotator cuff construct was frozen at −80° C. (−1° C./minute). Prior to surgical implantation, constructs were retrieved from the freezer and allowed to thaw in a 4° C. fridge for a minimum of one hour. After complete thawing of the construct, it was used for implantation.

Example 2. Implantation of the Engineered Tendon Graft Rotator Cuff (ETG-RC)

Figures 2A, 2B, 2C, 2D, 2E, 2F:
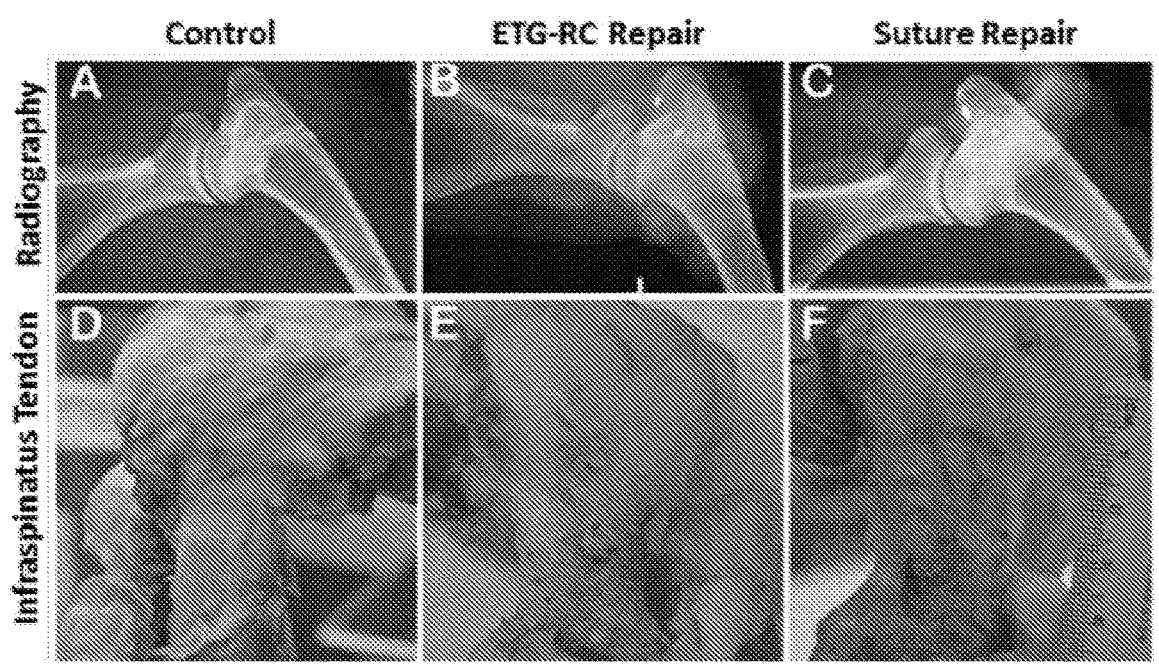
FIGS. 2A-2F show radiography and gross morphology of the enthesis of rotator cuffs from sheep following repair surgery and a 6-month recovery period. Radiographs of the shoulder joint showed appropriate and consistent anchor placement with no significant degradation of the rotator cuff joint in either of the surgical groups (FIGS. 2A-2C). Gross view of representative infraspinatus tendons from each group on day of necropsy (FIGS. 2D-2F).

Implantation of the scaffold-free, 3D tissue ETG-RC was performed in sheep. Surgery was performed to implant the construct in combination with a double row suture repair technique for repair of the infraspinatus tendon in a rotator cuff tear-repair procedure. Firstly, the construct was pulled through tendon, a baseball stitch and extra suture was used to secure the construct ends, allowing for passage of the three-prong end into the to the tendon and into the bone tunnel followed by fixation onto the periosteum and tendon. Control animals for this experiment were a suture-only repair without implantation of the tendon graft construct. All repairs were compared to the non-repaired contralateral leg. Following a six month recovery period, rotator cuffs of control (FIGS. 2A &2D) and explant grafted (FIGS. 2B &2E) and suture only (FIGS. 2C&2F) sheep were imaged by X-Ray (FIGS. 2A-2C) and gross morphology (FIGS. 2D-2F) to visualize the presence of construct and repair of the rotator cuff. Compared to the contralateral control side, the x-ray of the repaired tendon did not show any significant degradation to the rotator cuff joint in either the ETG-RC and Suture repairs. Gross morphology shows that while both surgical techniques resulted in tissue formation at the rotator cuff tendon, the ETG-RC showed normal tissue regeneration while the suture repair showed scar formation.

Example 3. Biomechanical Evaluation of the ETG-RC

Figure 3:
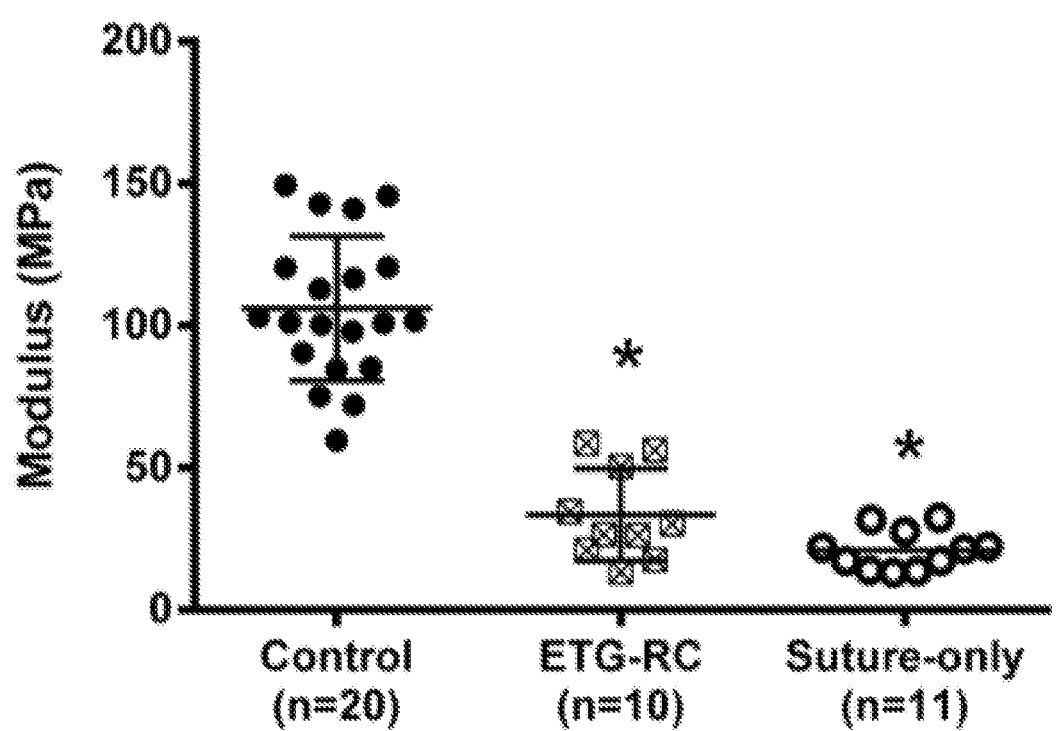
FIG. 3 shows the biomechanical testing of control and repaired tendon rotator cuffs of sheep tangent modulus. The mean modulus of the tendon-bone interface was as follows: contralateral (106±24 MPa, n=20, P<0.0001 ETG-RC, P<0.0001 SO), ETG-RC repair (33±16 MPa, n=10, P=0.34), and suture-only repair (21±7 MPa, n=11, P=0.34).

Six months following implantation, control and grafted tendon rotator cuffs of sheep were biomechanically tested by measuring tangent modulus (FIG. 3).

Following 6 months of recovery, rotator cuff tears repaired with either ETG-RC or suture technique displayed no difference in tangent modulus between repair groups. However, both repair groups were significantly less stiff than contralateral shoulders. The mean modulus of the tendon-bone interface was as follows: contralateral (106±24 MPa, n=20, P<0.0001 ETG-RC, P<0.0001 SO), ETG-RC repair (33±16 MPa, n=10, P=0.34), and suture-only repair (21±7 MPa, n=11, P=0.34).

In tangent modulus tests, construct grafted sheep exhibited lower tangent modulus when compared with control sheep (33±16 MPa vs 106±24 MPa, respectively).

The moduli (Mpa) in the strain range of 0.075-0.09 of the repaired tendons were significantly less (p<0.001) than the control native tendon.

Example 4. Histological Evaluation of the ETG-RC

Gross morphology of the implant site and histological evaluation of the implant were also performed. Gross morphology indicated there was an increase in connective tissue at the repair site for both the ETG-RC and Suture groups. Compared to the contralateral control side, the repair sites were covered with a minimal amount of scar tissue in both the ETG-RC and Suture repairs. Compared to the contralateral control side, the repaired tendon was in general wider, longer and thicker in both the ETG-RC and Suture repairs. Radiographs showed no signs of degeneration of the rotator cuff for either the ETG-RC or the Suture groups.

Mason's Trichrome staining (Luna L. G. Mayer's Hematoxylin & Eosin Stain (H&E). Manual of histologic staining methods of the Armed Forces Institute of Pathology (ed). McGraw-Hill, New York; 1968) was used for assessment of the fibrocartilage region of the enthesis and also showed that the enthesis of ETG-RC repair is composed of graded zones that resemble native enthesis, but that the enthesis of suture repair did not have a graded structure, indicating less regeneration.

Picrosirius red (PSR) staining is commonly used to visualize collagen histologically in tissue sections (Vogel et al., Methods X 2:124-134, 2015; Lattouf et al., J Histochem Cytochem. 62:751-8, 2014). Staining was carried out according to manufacturer's protocol (Picrosirius Red Stain Kit, Polysciences, Inc., Warrington, Pa., Cat #24901-500).

Figures 4A, 4B, 4C, 4D:
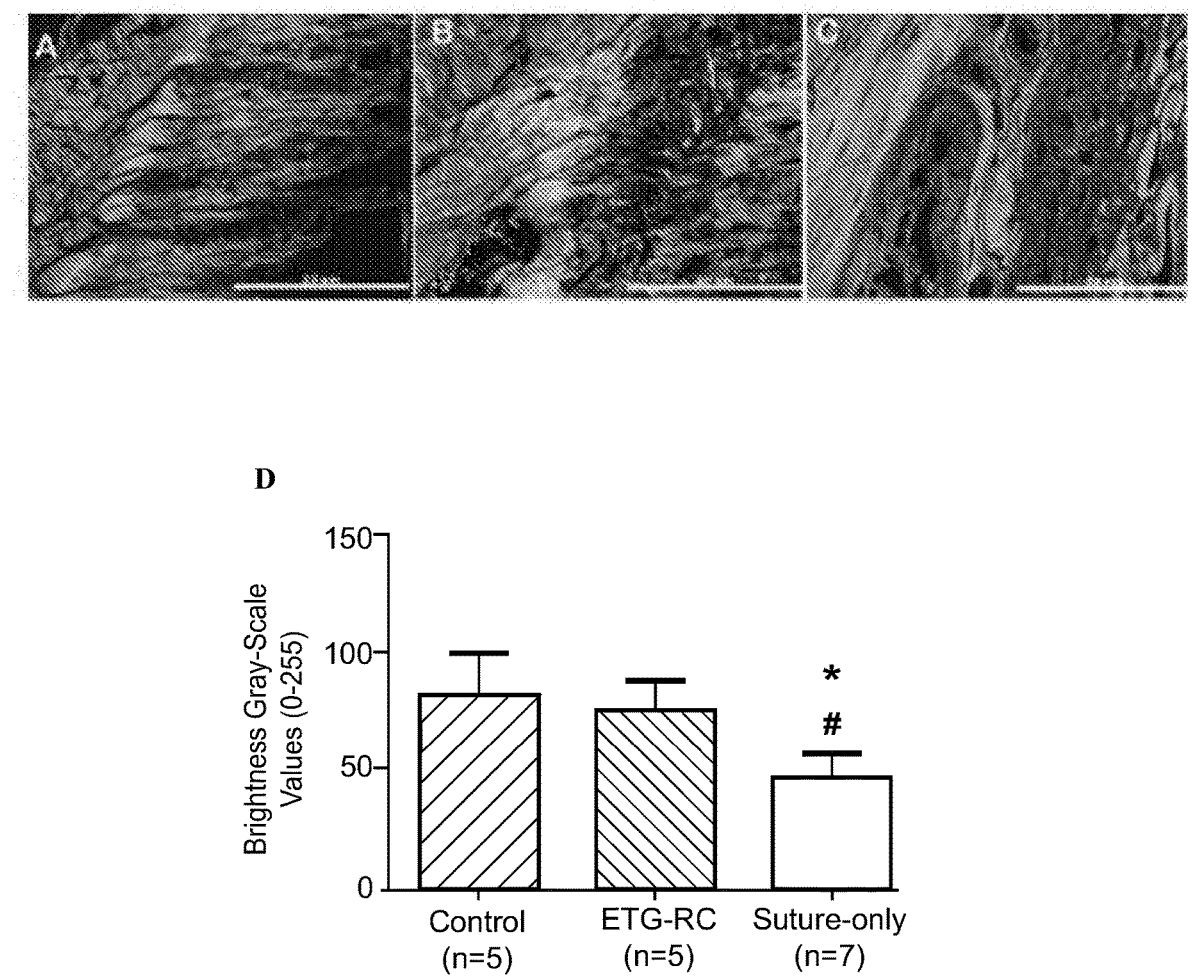

Picrosirius red staining was used to evaluate tissue collagen alignment at the enthesis interface. Collagen alignment showed that contralateral and ETG shoulders (FIG. 4B) had significantly greater alignment compared to suture-only (FIG. 4C) repaired shoulders. ETG-RC repaired shoulders were not significantly different than contralateral shoulders (FIG. 4A). Contralateral shoulders had an average brightness value of 81±18 gray scale units. ETG-RC repairs had a mean brightness gray scale value of 75±12, while suture only repairs had a value of 47±9 gray scale units (FIG. 4D). The increase in brightness intensity of ETG-RC repairs suggests an increase in remodeling of the collagen fiber architecture to a properly organized collagen fiber framework and resembles native enthesis. In contrast, the suture-only repair appears to be comprised of disorganized scar tissue at the interface. The amount of proteoglycan content was evaluated at the enthesis by determining the area of metachromasia of trichrome stained sections. No significant difference in area of fibrocartilage formation was observed in ETG-RC (FIG. 4F) or suture-only repairs (FIG. 4G), although suture-only repairs trended towards higher percent of metachromasia formation. The percent area of metachromasia, or fibrocartilage, at the enthesis for each group was as follows: contralateral shoulders (40±19), ETG-RC repairs (30±15), and suture only repairs (42±13) (FIG. 4H). Images also showed the linearity of the fibers that the structure of the enthesis is more amorphous in the suture-only repairs, while the ETG-RC has highly aligned fibers compared to control.

Hematoxylin and Eosin (H&E) staining (Luna L. G. Mayer's Hematoxylin & Eosin Stain (H&E). Manual of histologic staining methods of the Armed Forces Institute of Pathology (ed). McGraw-Hill, New York; 1968) staining was performed for qualitative morphological assessment of the repair. Both repair types demonstrated signs of regeneration indicated by vascularization and increased cellular density, however there were distinct phenotypic differences. H&E staining showed that the enthesis of ETG-RC repair (FIG. 4J) was generally composed of graded zones that resembled native enthesis structure (FIG. 4I). This zonal arrangement was not observed in the suture-only repairs (FIG. 4K), which had less fibrocartilage integration and fewer organized collagen fibers than ETG-RC and contralateral shoulders. Overall, suture-only repaired shoulders were characterized by an abrupt boundary of scar-like tissue at the tendon-bone interface (FIG. 4K), and did not have a graded structure, indicating slow regeneration. Histology of a representative ETG-RC at higher magnification shows dense bands of linear collagen fibers and little to no calcium deposition.

Numerous modifications and variations of the invention as set forth in the above illustrative examples are expected to occur to those skilled in the art. Consequently only such limitations as appear in the appended claims should be placed on the invention.

What is claimed:

1. A rotator cuff repair construct that is a scaffold-free, tissue-engineered tendon construct derived from growing cells in culture that establishes native enthesis in vivo after implantation, comprising:
   i) a bone-fixation end, wherein the bone-fixation end comprises a single column of tendon tissue for fixation to bone in a tendon repair surgery and at the opposite end the column branches to form a tendon-fixation end of the tendon construct; and
   ii) a tendon-fixation end having two or more tendon prongs each having a free end for fixation to a tendon in a tendon repair surgery and at the opposite end the prong ends fuse to form one end of the bone-fixation end of the construct,
   wherein the bone-fixation end regenerates a native enthesis at the interface of the bone and the rotator cuff repair construct, wherein the native enthesis includes a fibrocartilage region having graded zones.

2. The rotator cuff repair construct of claim 1, wherein the bone-fixation end has a diameter of approximately 3-6 mm and wherein the diameter of each of the tendon-fixation end prongs is approximately 2-3 mm.

3. The rotator cuff repair construct of claim 1, wherein the bone-fixation end is from about 2-7 cm in length.

4. The rotator cuff repair construct of claim 1, wherein the length of each of the tendon-fixation end prongs is approximately 1-5 cm.

5. The rotator cuff repair construct of claim 1, wherein the tendon-fixation end prongs start at about one-half (½) to two-thirds (⅔) of the length of the entire construct.

6. The rotator cuff repair construct of claim 1, wherein the tendon-fixation end has 2, 3, 4 or 5 prongs.

* * * * *